(12) United States Patent
Bruder et al.

(10) Patent No.: US 8,600,137 B2
(45) Date of Patent: Dec. 3, 2013

(54) ITERATIVE CT IMAGE RECONSTRUCTION WITH A FOUR-DIMENSIONAL NOISE FILTER

(75) Inventors: Herbert Bruder, Höchstadt (DE); Rainer Raupach, Heroldsbach (DE); Karl Stierstorfer, Österreicher (DE)

(73) Assignee: Siemens Aktiengesellschaft, Munich (DE)

( * ) Notice: Subject to any disclaimer, the term of this patent is extended or adjusted under 35 U.S.C. 154(b) by 333 days.

(21) Appl. No.: 13/111,244

(22) Filed: May 19, 2011

(65) Prior Publication Data
US 2011/0293159 A1    Dec. 1, 2011

(30) Foreign Application Priority Data
Jun. 1, 2010   (DE) .................... 10 2010 022 306

(51) Int. Cl.
*G06K 9/00*   (2006.01)
(52) U.S. Cl.
USPC ........................................................ 382/131
(58) Field of Classification Search
USPC ........ 382/128, 131; 250/363.04; 378/4, 5, 11, 378/21
See application file for complete search history.

(56) References Cited

U.S. PATENT DOCUMENTS

| | | | |
|---|---|---|---|
| 7,181,084 B2 | 2/2007 | Jostschulte | |
| 8,175,359 B2 * | 5/2012 | O'Halloran et al. | 382/131 |
| 2003/0086105 A1 | 5/2003 | Jostschulte | |
| 2005/0135664 A1 * | 6/2005 | Kaufhold et al. | 382/131 |
| 2006/0171578 A1 * | 8/2006 | Novak | 382/131 |
| 2007/0019851 A1 * | 1/2007 | Nishide et al. | 382/131 |
| 2007/0081704 A1 * | 4/2007 | Pan et al. | 382/128 |

(Continued)

FOREIGN PATENT DOCUMENTS

| | | |
|---|---|---|
| DE | 10146582 A1 | 4/2003 |
| DE | 102007061935 A1 | 6/2009 |
| DE | 102009039987 A1 | 3/2011 |

OTHER PUBLICATIONS

4D Iterative Image Filter for Noise Reduction at Maintained Temporal Resolution in Cardiac CT RSNA2009, Chicago, Session: Physics (CT: New Methods), Nov. 29, 2009, Dr. T. Flohr, H. Bruder, R. Raupach, K. Stierstorfer, T. Flohr, Siemens, Healthcare Division, Forchheim, Germany, e-mail: herbert.bruder@siemens.com; Others; 2009; US.

(Continued)

*Primary Examiner* — Shervin Nakhjavan
(74) *Attorney, Agent, or Firm* — Harness, Dickey & Pierce, P.L.C.

(57) ABSTRACT

A method is disclosed for reconstruction of image data of an object under examination from measurement data, with the measurement data having been captured during a relative rotational movement between a radiation source of a computed tomography system and the object under examination. In at least one embodiment, first image data is computed by the measurement data being modified to obtain a specific gray value characteristic of the first image data to be reconstructed and the first image data is computed by way of an iterative algorithm using the modified measurement data. Second image data is also computed by a series of chronologically-consecutive images being reconstructed and processing being carried out on the series of images to reduce temporal noise. Finally a combination of the first and the second image data is carried out.

20 Claims, 4 Drawing Sheets

(56) References Cited

U.S. PATENT DOCUMENTS

| | | | |
|---|---|---|---|
| 2009/0161935 A1 | 6/2009 | Bruder et al. | |
| 2010/0086185 A1* | 4/2010 | Weiss | 382/131 |
| 2010/0309198 A1* | 12/2010 | Kauffmann | 345/419 |
| 2011/0037761 A1* | 2/2011 | Mistretta et al. | 345/419 |
| 2011/0038517 A1* | 2/2011 | Mistretta et al. | 382/128 |
| 2011/0052030 A1 | 3/2011 | Bruder et al. | |

OTHER PUBLICATIONS

J. Sunnegardh et al.: "Regularized iterative weighted filtered backprojection for helical cone-beam CT", Med. Phys. vol. 35, Sep. 2008, p. 4173-4185; Others; 2008.

German Priority application DE 10 010 022 306.9 filed June 1, 2010 and not yet published.

* cited by examiner

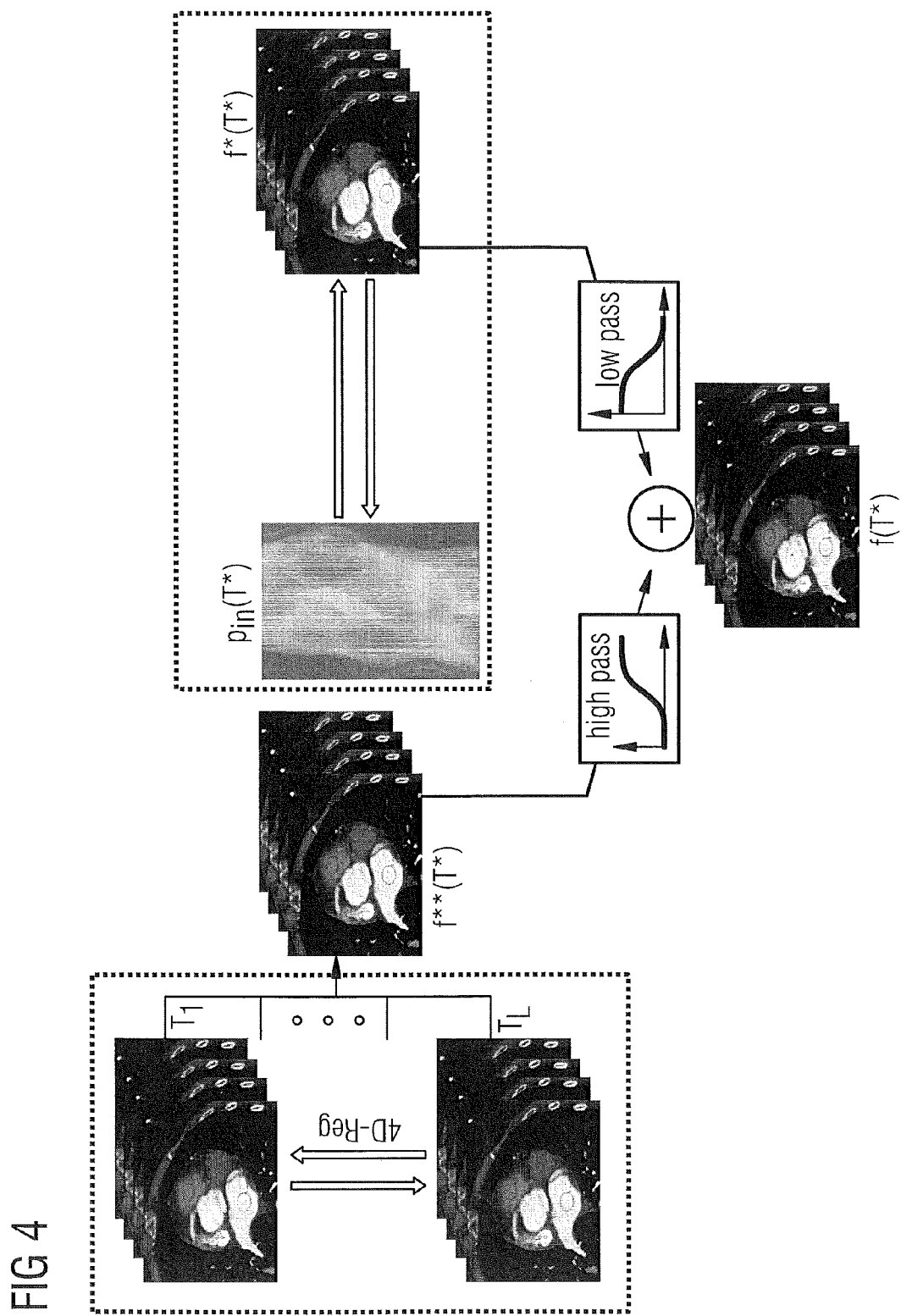

ITERATIVE CT IMAGE RECONSTRUCTION WITH A FOUR-DIMENSIONAL NOISE FILTER

PRIORITY STATEMENT

The present application hereby claims priority under 35 U.S.C. §119 on German patent application number DE 10 2010 022 306.9 filed Jun. 1, 2010, the entire contents of which are hereby incorporated herein by reference.

FIELD

At least one embodiment of the invention generally relates to a method for the reconstruction of picture data of an object under examination from measurement data, with the measurement data having been captured beforehand during a relative rotational movement between a radiation source of a computed tomography system and the object under examination.

BACKGROUND

Tomographic imaging methods are characterized by enabling the internal structures of an object under examination to be examined without having to carry out operational interventions on said structures. One possible type of tomographic imaging consists of capturing a number of projections from different angles. A two-dimensional slice image or a three-dimensional volume image of the object under examination can be computed from these projections.

Computed tomography is an example of this type of tomographic imaging method. Methods for scanning an object under examination with a CT system are generally known. Typical methods employed in such cases are orbital scans, sequential orbital scans with advance or spiral scans. Other types of scans which are not based on orbital movements are possible, such as scans with linear segments for example.

Absorption data of the object under examination is recorded from different imaging angles with the aid of at least one X-ray source and at least one detector lying opposite said source and this absorption data or projections collected in this way are computed by way of appropriate reconstruction methods into image slices through the object under examination.

For reconstruction of computed-tomographic images from X-ray CT datasets of a computed-tomography (CT) device, i.e. from the captured projections, what is known as a Filtered Back Projection (FBP) is used nowadays as the standard method. After the data has been recorded, a so-called "rebinning" step is executed in which the data generated with the beam spreading out in the form of a fan is rearranged such that it is available in a form such as would occur had the detector been hit by X-rays arriving at the detector in parallel. The data is then transformed into the frequency range. A filtering is undertaken in the frequency range and subsequently the filtered data is back transformed. With the aid of the data sorted out and filtered in this way a back projection is then carried out onto the individual voxels within the volume of interest. However, because of the approximative way in which they operate, problems arise with the classical FBP methods with so-called cone-beam artifacts and spiral artifacts. Furthermore image sharpness is coupled to image noise in classical FBP methods. The higher is the sharpness obtained, the higher is also the image noise, and vice versa.

Iterative reconstruction methods have thus been recently developed, with which at least some of these limitations can be overcome. In such an iterative reconstruction method initial image data is first reconstructed from the projection measurement data. A folding back projection method can typically be used for this purpose. Synthetic projection data is then generated from this initial image data using a "projector", which is designed to map the measuring system as well as possible.

The difference from the measurement signals is then back projected with the operator adjoined to the projector and a residuum image is reconstructed with which the initial image is updated. The updated image data can be used in its turn to generate new synthetic projection data in the next iteration step with the aid of the projection operator, to once again form the difference from the measurement signals from said data and to compute a new residuum image with which the image data of the current iteration step can again be improved etc. Such a method enables image data to be reconstructed which exhibits relatively good image sharpness yet still produces low-noise images. Examples of iterative reconstruction methods are algebraic reconstruction technique (ART), simultaneous algebraic reconstruction technique (SART), iterated filtered back projection (IFBP), or also statistical iterative image reconstruction techniques.

SUMMARY

In at least one embodiment of the invention, a method for reconstruction of CT images is demonstrated which employs at least one technique, such as an iterative algorithm. Furthermore at least one embodiment is directed to a corresponding control and processing unit, a CT system and/or a computer program product.

At least one embodiment is directed to a method, a control and processing unit, a CT system, a computer program and/or a computer program product. Advantageous embodiments and developments are the subject matter of subclaims.

In at least one embodiment of the inventive method the reconstruction of image data of an object under examination from measurement data, this data has previously been captured in a relative rotational movement between a radiation source of a computed tomography system and the object under examination. First and second image data is computed. The first image data is computed by the measurement data for achieving a specific gray value characteristic of the first image data to be reconstructed being modified and the first image data being computed by means of an iterative algorithm using the modified measurement data. The second image data is computed by a series of chronologically-consecutive images being reconstructed and the processing of the sequence of images to reduce the temporal noise being undertaken. Finally a combination of the first and the second image data is carried out.

The image data to be computed by a combination of the first and second image data can involve two-dimensional image slices or three-dimensional volume images of the object under examination. The same also applies for the first and second image data.

The first image data is computed iteratively. A number of iterations i.e. at least two take place, with image data of the current iteration being computed from image data of the previous iteration in each iteration. For iteration zero the image data is determined from the measurement data or from the modified measurement data.

To compute the first image data the measurement data is modified. This modification is such that the first image data available after the iterative reconstruction exhibits a specific gray value characteristic. This gray value characteristic corresponds to a texture or a frequency characteristic of the first image data. Preferably the specific gray value characteristic is selectable, i.e. a well-defined gray value characteristic can be selected which the reconstructed image data exhibits.

To calculate the second image data a number of images are first reconstructed. These images relate to different points in time. The point in time to which an image relates is produced from the measurement data included for image reconstruction. This measurement data is captured during a specific time segment. The mid or other point in time within this time segment can be assigned to the image as its image time. Synonymous with the assignment of a point in time is of course the assignment of the time segment of the measurement data capture.

The practice of carrying out processing which reduces local noise in a CT image is known. This corresponds to a smoothing of the image and is carried out by applying a suitable filter function to the image. Deviations within a CT image between pixel values of different pixels are thus smoothed out by this method. If a series of consecutive CT images is present, noise reduction processing is also possible in the time dimension. Using this method, deviations of a pixel value of an image from the corresponding pixel values of the corresponding pixel of images of one or more other points in time are thus smoothed out. The second image data is obtained by such processing of the series of images to reduce temporal noise.

Neither the first nor the second image data is output as the result image. Instead a combination of the first and the second image data is produced. Before this combination further processing steps relating to the first and/or the second image data can be carried out.

In a development of at least one embodiment of the invention, during the computation of the first image data in the iterations no computation step for noise reduction is employed. In the known iterative CT image reconstruction methods, a so-called regularization term is used which, for each iteration, partly frees the currently computed iteration image of noise by smoothing. This computation step is dispensed with in the method for computing the first image data. I.e. the computing specification for computing the iteration image from the image data of the last iteration does not contain such a component. The absence of the noise reduction in the iterations can be compensated for at least partly by the measurement data being modified and being subsequently used for computing the iteration images.

In accordance with the development of at least one embodiment of the invention the first image data relates to a specific point in time, the series of chronologically-consecutive images to a number of points in time, including the specific point in time, and the second image data also to the specific point in time. Thus there is a point in time for which both the first and also the second image data is available. Accordingly the image data resulting from the combination of the first and second image data relates to this point in time. For an object under examination which is moving the point in time is preferably that point in time at which movement is minimal. For the computation of the second image data initially images of a number of points in time are available, from which, through processing to reduce the temporal noise, image data of an individual point in time is obtained.

It is especially advantageous for the series of chronologically-consecutive images to be computed by way of a non-iterative image reconstruction algorithm. Such algorithms, e.g. FBP, have the advantage over iterative image reconstructions of being able to be executed less computer-intensively and thereby more quickly.

According to an embodiment of the invention a CT convolutional kernel predetermining the specific gray value characteristic is used in the calculation of the first image data for the modification of the measurement data. This enables it to be ensured that at the output of the iteration loop there is image data with a well-defined texture. Such CT convolutional kernels are known for example from conventional FBP image reconstruction. Examples are as follows: body kernel B30, cranium kernel H40. In particular the CT convolutional kernel can be employed in the form of its modulation transmission function.

It is especially advantageous for the specific gray value characteristic to be adapted to the gray value characteristic of the second image data. The reason for this is that the first and the second image data are to be combined. Such a combination generally only leads to sensible results if the gray value characteristics of the two image datasets correspond to each other in some way. To make the first image data, i.e. the image data of the iterative reconstruction thus compatible with the second image data, the iterative reconstruction is undertaken such that the specific gray value characteristic is present as the initial image. This is brought about by the characteristics of the modified image data.

In an embodiment of the invention the processing reducing the temporal noise comprises a four dimensional non-linear filtering. Four dimensional means here that the noise reduction is carried out both in the dimension of the place, which is assumed to be three-dimensional and also in the further dimension of the time. An edge-retaining smoothing is possible through the non-linearity. In the dimension of the place such smoothing does not occur evenly over the entire image; instead it is smoothed preferably in homogeneous image regions, while smoothing is very largely dispensed with in image regions with edges. In this way the smoothing is edge-retaining. In the dimension of time such smoothing is not undertaken evenly over each of the changes between images of different points in time. Instead a distinction can be made as to whether a change was caused by movement or by noise, with smoothing only preferably being undertaken in relation to noise.

In a development of at least one embodiment of the invention, the first image data is subjected to lowpass filtering and the second image data to highpass filtering before the combination. This makes it possible to select the advantageous properties of the first and the second image data and to transfer these into the combination image data. Accordingly the negative properties of the second image data are located in the region of lower frequencies.

The combination of the image data can be carried out both in the frequency area and also in the location area. For a combination in the frequency area a Fourier transformation of the first and second image data from the location area into the frequency area is first undertaken, after which the combination is carried out with an inverse Fourier transformation from the frequency area into the location area being undertaken thereafter.

Preferably the first and the second image data is added pixel-by-pixel for combination. This addition can be undertaken weighted or unweighted.

According to an embodiment of the invention image data is first computed in the iterative algorithm from the original measurement data and image data of the following iterations is computed using the modified measurement data. This means that the unmodified image data is only used for computing iteration image zero, while in the following iterations only the modified measurement data is employed for image computation.

It is advantageous if, in the iterative algorithm, measurement data is computed in each iteration from computed measurement data and is compared with the modified measurement data. The use of the modified measurement data thus serves for comparison with synthetic, i.e. computed measurement data. This can be implemented by a simple or weighted differentiation. The object of the iterative algorithm is to reconstruct the first image data such that measurement data computed from it matches the modified measurement data as well as possible. From the comparison correction data can then be computed and used for correcting the image data.

In at least one embodiment, the inventive control and processing unit is used for reconstruction of image data of an object under examination from measurement data of a CT system. It comprises a program memory for storing program code—with program code being present therein—if necessary among other data, which is suitable for executing a method of the type described above or for bringing about or controlling this execution. At least one embodiment of the inventive CT system comprises such a control and processing unit. It can also contain other components, which are needed for example for capturing measurement data.

The inventive computer program of at least one embodiment has program code which is suitable for executing the method of the type described above when the computer program is executed on a computer.

The inventive computer program product of at least one embodiment comprises program code stored on a computer-readable data medium which is suitable for carrying out the method of the type described above when the computer program is executed on a computer.

BRIEF DESCRIPTION OF THE DRAWINGS

The invention will be explained below on the basis of an example embodiment. The figures show:

FIG. 4: a flow diagram for reconstruction of a CT image,

DETAILED DESCRIPTION OF THE EXAMPLE EMBODIMENTS

Figure 1:
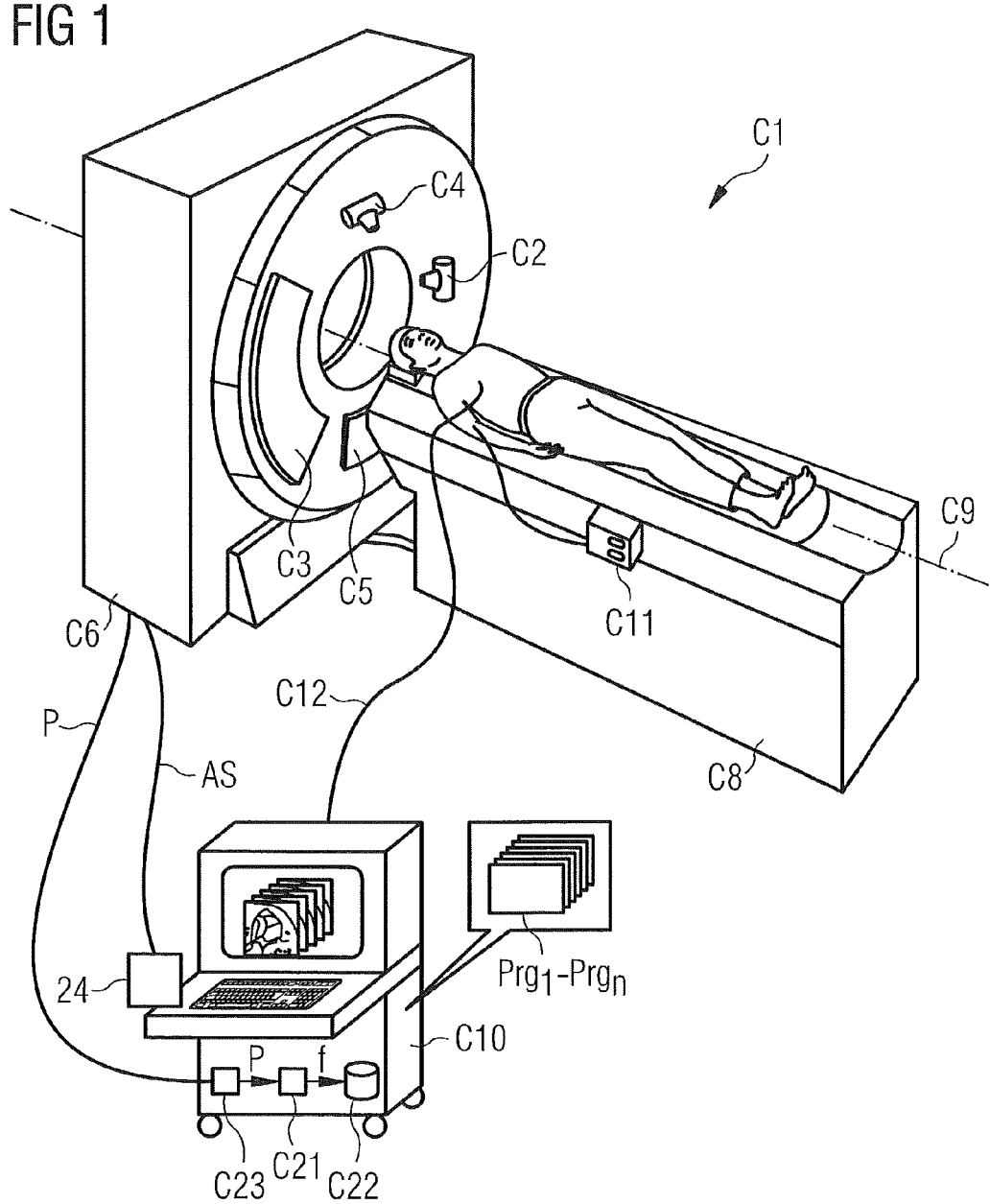
FIG. 1: a first schematic diagram of an example embodiment of a computed tomography system with a image reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 initially shows a schematic diagram of a first computed-tomography system C1 with a image reconstruction device C21. This involves what is known as a third-generation CT device, to which embodiments of the invention are not restricted however. Located in the gantry housing C6 is a closed gantry not shown in the diagram on which are arranged a first X-ray tube C2 with a detector C3 lying opposite it. Optionally arranged in the CT system shown here are a second x-ray tube C4 with a detector C5 lying opposite it, so that a higher temporal resolution can be achieved by the radiator/detector combination additionally available, or with the use of different X-ray energy spectra in the radiator/detector system, dual-energy examinations can be undertaken.

The CT system C1 also comprises a patient couch C8 on which the patient can be pushed during the examination along a system axis C9, also referred to as the z-axis, into the measurement field, with the scanning itself able to occur both as a pure orbital scan without forward movement of the patient exclusively in the region of interest under examination. The movement of the patient couch C8 relative to the gantry is effected by a suitable motorization. In this case the X-ray source C2 or C4 respectively rotates around the patient. In such cases the detector C3 or C5 respectively moves in parallel in relation to the X-ray source C2 or C4 in order to capture projection measurement data which is then used for reconstruction of image slices.

As an alternative to a sequential scan in which the patient is pushed step-by step between the individual scans through the examination field, there is naturally also the option provided of a spiral scan, in which the patient is pushed continuously during the orbital scanning with the x-rays along the system axis C9 through the examination field between x-ray tube C2 or C4 respectively and detector C3 or C5 respectively. The movement of the patient along the axis C9 and the simultaneous orbital movement of the X-ray source C2 or C4 respectively produces a helical track for a spiral scan for the x-ray source C2 or C4 relative to the patient during the measurement. This track can also be achieved by the gantry being moved along the axis C9 while the patient does not move. It is also possible to move the patient continuously and periodically backwards and forwards between two points.

The CT system 10 is controlled by a control and processing unit C10 with a computer program code $Prg_1$ to $Prg_n$ present in a memory. It should be noted that these computer program codes $Prg_1$ to $Prg_n$ can naturally also be contained on an external storage medium and loaded in the control and processing unit C10 as required.

From the control and processing unit C10 acquisition control signals AS can be transmitted via a control interface 24 in order to control the CT system C1 in accordance with specific measurement protocols. The acquisition control signals AS relate in such cases to the X-ray tubes C2 and C4, with specifications able to be given about their power and the times at which they are switched on and switched off, as well as the gantry, with specifications able to be provided about its speed of rotation as well as the advance of the couch.

Since the control and processing unit C10 has an input console, measurement parameters can be entered by a user or operator of the CT device C1 which then control the data capture in the form of acquisition control signals AS. Information about measured parameters currently used can be shown on the screen of the control and processing unit C10; in addition further information relevant for the operator can be displayed.

The projection measurement data p or raw data acquired by detector C3 or C5 is transferred via a raw data interface C23 to the control and processing unit C10. This raw data p is then, if necessary after suitable pre-processing, further processed in an image reconstruction component C21. The image reconstruction component C21 is realized in this example embodiment in the control and processing unit C10 in the form of software on a processor, e.g. in the form of one or more of the computer program codes $Prg_1$ through $Prg_n$. What has already been stated in relation to image reconstruction applies in relation to the control of the measurement process, that the computer program codes $Prg_1$ to $Prg_n$ can also be contained on an external storage medium and can be loaded if necessary into the control and processing unit C10. It is also possible for the control of the measurement process and the image reconstruction to be carried out by different processing units.

The image data f reconstructed by the image reconstruction component C21 is then stored in a memory C22 of the control and processing unit C10 and/or output in the usual way on the screen of the control and processing unit C10. It can also be fed via an interface not shown in FIG. 1 into a network connected to the computed-tomography system C1, for example a radiological information system (RIS) and stored in mass storage accessible in this system or output as images.

The control and processing unit C10 can additionally also execute the function of an EKG, with a line C12 being used for deriving the EKG potentials between patient and control and processing unit C10. In addition the CT system C1 shown in FIG. 1 also has a contrast media injector C11 via which additional contrast media is injected into the blood circulation of the patient so that the blood vessels of the patient, especially the heart chambers of the beating heart, can be better represented. In addition there is also the opportunity of carrying out perfusion measurements for which the suggested method is likewise suitable.

Figure 2:
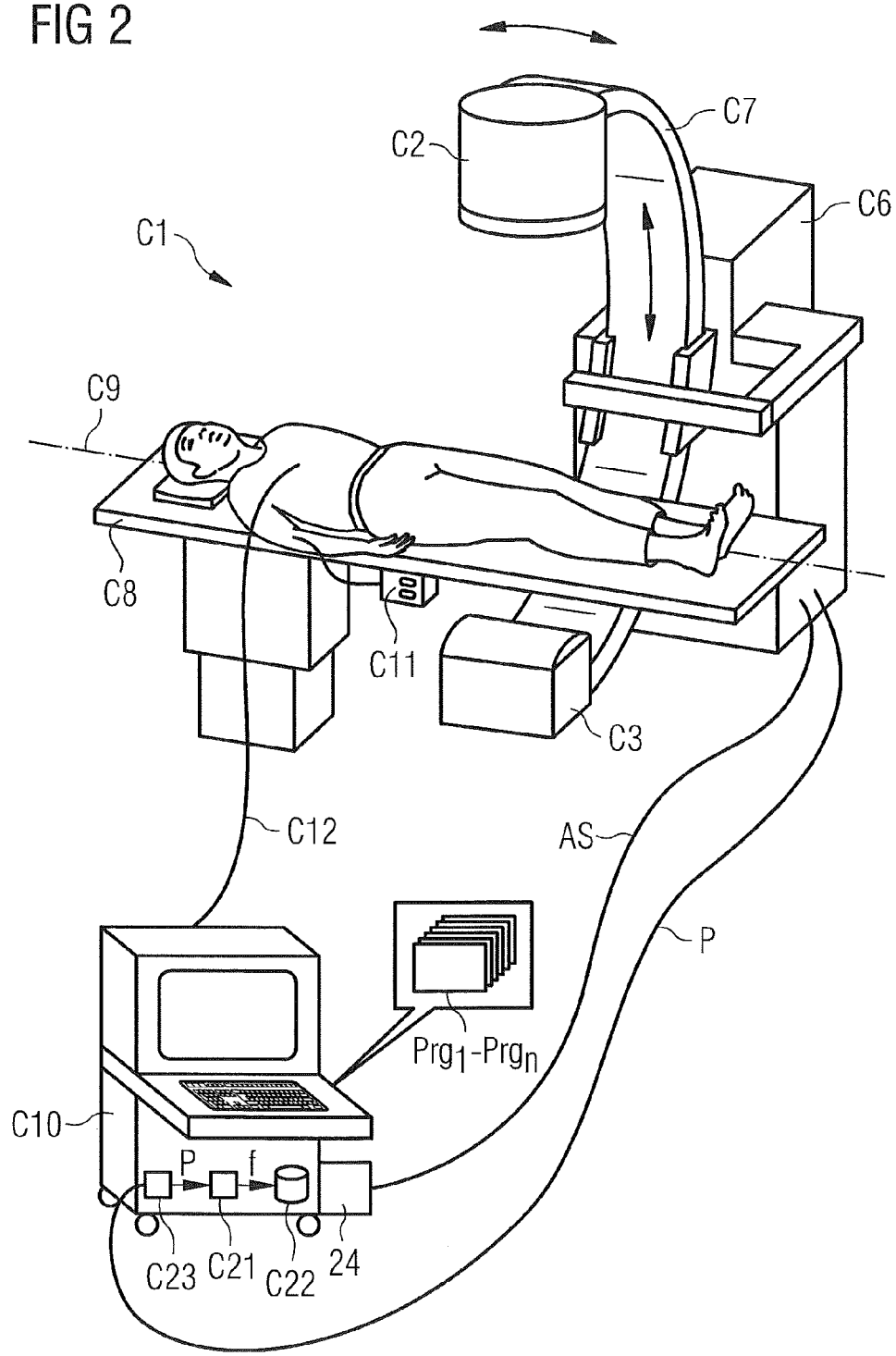
FIG. 2: a second schematic diagram of an example embodiment of a computed tomography system with a image reconstruction component.

FIG. 2 shows a C-arm system, in which, by contrast with the CT system of FIG. 1, the housing C6 carries the C-arm C7, to one side of which is attached the x-ray tube C2 and to the opposite side the detector C3. The C-arm C7 is likewise hinged around a system axis C9 for a scan, so that a scan can be undertaken from a plurality of scanning angles and corresponding projection data p can be determined from a plurality of projection angles. The C-arm system C1 of FIG. 2, like the CT system from FIG. 1, has a control and processing unit C10 of the type described for FIG. 1.

An embodiment of the invention is able to be used in both of the systems shown in FIGS. 1 and 2. Furthermore it is basically also able to be used for other CT systems, e.g. for CT systems with a detector forming a complete ring.

A description is given below of how CT images can be obtained by way of an iterative image reconstruction algorithm.

In conventional non-iterative image reconstruction methods so-called cone beam artifacts and also spiral artifacts occur in the CT image. Cone beam artifacts arise because the individual slices, i.e. the different detector rows are assumed to be lying in parallel with each other for the image reconstruction while in reality they are tilted towards one another. This effect increases as the number of detector rows increases. By contrast spiral artifacts are produced by data interpolation which is necessary for spiral scanning in conventional reconstruction algorithms in order to have data available for all z-positions and angles of rotation of the X-ray tube.

An advantage of iterative reconstruction methods compared to conventional non-iterative procedures such as FBP (Filtered BackProjection) for example is that the cone beam and spiral artifacts described do not occur in a CT image which has been iteratively reconstructed. Furthermore the image noise is also reduced compared to images reconstructed in a conventional manner. These two positive effects are however achieved at different points in time in the course of iterative computation; it has been shown that with iterative reconstruction in the image artifacts are already removed after a few, e.g. 2, iteration cycles, while a convergence of image noise is only achieved after further iteration cycles.

In an iterative reconstruction the measurement data $p_{in}$ is used as the input signal, which typically is available in semi-parallel cone beam geometry, i.e. after azimuthal parallel rebinning. First of all a reconstruction of initial image data $f_0$ is undertaken from the projection measurement data $p_{in}$ by means of the back projection operator $Q^T$. A folded back projection method is used for this purpose for example. From this initial image data $f_0$, with a projector Q, a projection operator which is designed to emulate the measurement process mathematically as well as possible, synthetic projection data $p_{syn}$, is generated. The difference between the synthetic projection data $p_{syn}$ and the measurement data $p_{in}$ is then back projected with a back projection operator $Q^T$ adjoined to the projector Q and in this way a residuum or correction image $f_{corr}$ is reconstructed with which the initial image $f_0$ is updated. In this way the image $f_1$ of the first iteration is obtained. This updated image data $f_1$ can in its turn be used to generate new synthetic projection data $p_{syn}$ in a next iteration step with the aid of the projection operator Q, to form the difference from the measurement signals $p_{in}$ again from this and to compute a new residuum image $f_{corr}$ with which the image data $f_1$ of the current iteration step is again improved and thus the image data $f_2$ of the next iteration step is obtained etc.

To supplement this basic mechanism in iterative image reconstruction a so-called regularization term is also normally used in iterative image reconstruction, which reduces the image noise and determines its behavior. The regularization term is used in addition to the correction image in each iteration cycle, which brings about a noise averaging and a stabilization of the solution and thereby a convergence of the iterative algorithm.

For an iterative reconstruction based on a filtered back projection (FBP) the update equation for the three-dimensional image volume f is given by:

$$f_{k+1} = f_k + [\alpha \cdot Q^T \cdot K \cdot (Q \cdot f_k - p_{in}) - \gamma R(f_k)] \quad \text{Formula (1)}$$

In this case $f_{k+1}$ is the image of the K+1th iteration which is computed from the image $f_k$ of the kth iteration.

The correction term—this corresponds to the correction image $f_{corr}$—is $\alpha \cdot Q^T \cdot K \cdot (Q \cdot f_k - p_{in})$. $\alpha$ is a constant factor here which determines the strength of the correction of the image $f_k$ by the correction image $f_{corr}$. A Ramlak core (linear ramp in frequency space) is usually selected as the core K. The correction term corrects image errors which are caused by the non-exact back projector $Q^T$.

The correction term corresponds to a highpass filtering of the image $f_k$. For this reason the correction term brings about an increase in image noise. This is countered-by the regularization term. Without the use of the regularization term the image noise would thus increase from iteration to iteration. The regularization term is $\gamma \cdot R(f_k)$, with $\gamma$ representing a constant factor which determines the strength of the admixture of the regularization term. $R(f_k)$ is a non-linear highpass filter which is applied to the image $f_k$ of the kth iteration step. In the update equation, because of the minus sign, the effect of the regularization term is like that of a non-linear lowpass.

If one considers the formula (1), a component is present with the correction term which includes a switch of the image data into the measurement data space. This is compute-intensive because of the necessary forwards and backwards projection computations and therefore expensive in terms of resources and time. By contrast a component is included with the regularization term which corresponds to pure manipulation in the image data space, which is less effort in computing terms.

The function of the correction term is to rectify image errors while the regularization term brings about a noise reduction of the image. As already explained, the aim of removing the image errors is generally achieved with far fewer iterations than the removal of noise from the image. However each iteration requires significant computing effort so that it would be advantageous to exit from the iteration loop after rectification of the image errors.

Figure 3:
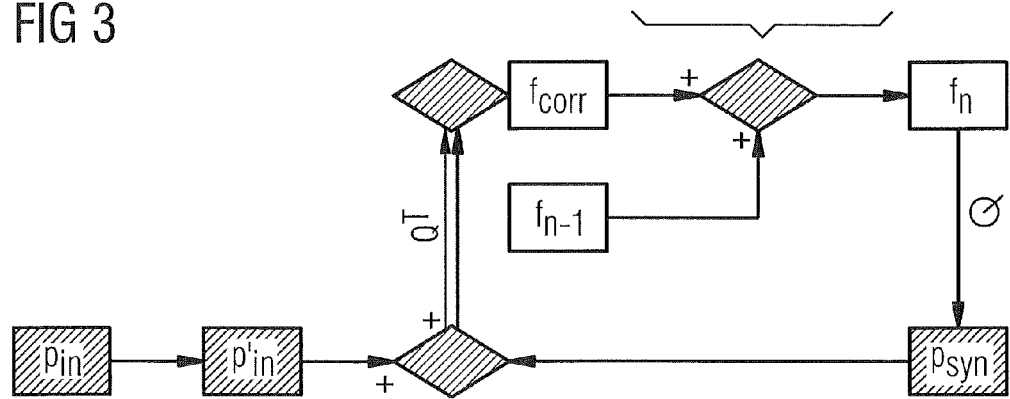
FIG. 3: a flow diagram of the iterative image reconstruction.

Thus, as shown in FIG. 3, the iterative algorithm is applied without using the regularization term. Thus $$f_{k+1} = f_k + \alpha \cdot Q^T \cdot K \cdot (Q \cdot f_k - P_{in}') \quad \text{Formula (2)}$$

is used as the update equation.

From the measurement data $p_{in}$ the initial image $f_0$ is computed as explained above. For calculating each correction image $f_{corr}$, not the measurement data $p_{in}$ but modified measurement data $P_{in}'$ obtained from said data is used, the function of which will be explained in greater detail below. At the point at which the brace is shown the regularization term in accordance with formula (1) would normally be used, which is dispensed with in accordance with formula (2).

As already mentioned, because of its highpass effect, the correction term increases the image noise from iteration to iteration, so that by mere omission of the regularization term by the iterative algorithm no defined image noise of the resulting image can be brought about. Thus the iterative algorithm in accordance with formula (2) should be noise-neutral; this means that the increase in noise is avoided by the correction term. This occurs by the measured values $p_{in}$ being filtered two-dimensionally in accordance with formula (3). The measured values $p_{in}$ are available here for each projection angle in two-dimensional form, corresponding to the two-dimensional detector, the extent of which stretches in the channel and row direction.

$$P_{in}' = ((Q \cdot Q^T)_{xy} \cdot I/K) \otimes (Q \cdot Q^T)_z \cdot p_{in} \quad \text{Formula (3)}$$

$(Q \cdot Q^T)$ identifies the transversal component, i.e. the component acting in the channel direction or within the plane of a slice of the object under examination, and $(Q \cdot Q^T)_z$ the axial component, i.e. the component of the three-dimensional operator $(Q \cdot Q^T)$ acting in the row direction z or perpendicular to the slice plane. This operator $(Q \cdot Q^T)$ essentially characterizes the interpolation functions in the forward and back projection. The back projection is typically voxel-driven i.e. the detector signal assigned to a voxel must be determined by (e.g. linear) interpolation. Equally the image signals must be interpolated voxel-by-voxel (linearly) in the projection of the image signal for calculating the line integral. $(Q \cdot Q^T)_{xy}$ and $(Q \cdot Q^T)_z$ act as lowpasses; in both cases the filter is a short-range filter.

Operator I is a CT convolutional kernel able to be predetermined by a user, i.e. by the person analyzing the CT image, usually a radiologist. With a filtered back projection such a CT filter core is applied in the filter step; this determines the noise characteristic of the resulting image. Also in the present iterative algorithm the CT filter core I determines the noise characteristic of the image output by the iterative algorithm. The expression I/K corresponds to the modulation transmission function of the CT imaging. I.e. in addition to the lowpass filtering explained above, the input signal is lowpass filtered with the modulation transmission function of the input core I.

$P_{in}'$ is thus a lowpass filtered version of the measurement data $p_{in}$ with a specific frequency characteristic specified by the core I.

In the correction term, in accordance with formula (2), the synthetic data $p_{syn}$ is not compared to the measurement data $p_{in}$, but to the modified measurement data $P_{in}'$. Because of the properties of the modified measurement data $P_{in}'$ the effect of this on the one hand is that no increase of noise in the iteration image is brought about by the correction image $f_{corr}$ and on the other hand that, after the last iteration, the result image exhibits the frequency characteristic or gray value characteristic specified by the operator I. Thus a dedicated and desired noise characteristic of the image present after the iteration has been aborted is forced by the use of the modified data $P_{in}'$.

By applying a suitable filter after ending of the iterative reconstruction a desired sharpness-to-noise-ratio of the image can be set. Nonlinear three-dimensional image filters are suitable for this. Advantageous is the use of a filter which on the one hand carries out a smoothing of the image in homogenous areas; this makes it possible to adjust the noise power spectrum and thus make a direct check on the desired gray value characteristic. On the other hand the filter can exclude non-homogenous areas in which a significant structure is available in the image from the smoothing, so that edges are left out of the smoothing. By using a suitable filter function it is even possible to enhance the edges. Overall such a filter causes an edge-retaining smoothing, i.e. a noise reduction, while simultaneously retaining or increasing the visibility of detailed information and sharpness. Such a filter can be applied either singly or iteratively to the image to be filtered.

A concrete example of such a filter is to be found in the author's subsequently published application DE 10 2009 039 987.9, the entire contents of which are hereby incorporated herein by reference. A filter function is reproduced in formula (8) of this application. This can also be employed simplified by only the term identified by II b and not the term identified by I being used. A further concrete example of such a filter, the contents of which largely correspond to the first-mentioned filter, was presented in a paper at the RSNA2009 in Chicago in the Session Physics (CT: New Methods) on Nov. 29, 2009 from 11:15-11:25 by Dr. T. Flohr. The entire contents of this paper are also hereby incorporated herein by reference.

The case in which spatiotemporal CT measurement data is available is considered below. This is typically the case in cardio CT, i.e. during imaging of the moving heart. Here measurement data is captured at a z-position at different points in time. These points in time are linked via the EKG measurement taking place simultaneously to the heart phases of the object under examination. Accordingly for a z-position, i.e. for a specific slice of the object under examination, CT images of different points in time or heart phases can be reconstructed. As a rule a point in time $T^*$ seen as optimal in respect of the heart movement can be selected and the CT image of volume corresponding to this point in time output as the result image. The point in time $T^*$ is in this case usually a heart phase with minimal movement, so that the coronary arteries will be presented largely movement-artifact-free.

CT images not only exhibit a specific noise within each image, caused especially by statistical processes in the x-ray source and in the detector; for a temporal sequence of images—this corresponds to the case of four-dimensional data capture—this noise also extends to the dimension of the time stop. If consecutive CT images have a sufficiently large temporal spacing, they are statistically uncorrelated. This is the case if disjunctive datasets are used for the images. This can be used for improving the image noise by a temporal noise averaging or smoothing being carried out.

The image volume reconstructed with the iterative algorithm in accordance with FIG. 3, which corresponds to the point in time $T^*$, is designated below by $f^*(T^*)$. This image volume $f^*(T^*)$ is, as already described above, largely free from reconstruction artifacts, i.e. from image artifacts which are caused by a non-exact reconstruction method. However the noise level is relatively high since there was no regularization with the iterative algorithm. In order to reduce this, as already explained, the method in accordance with formula (8) of the subsequently published application can be used. While formula (8) of this application relates to three-dimensional image filtering, i.e. the noise reduction related to an individual image, formula (11) shows how such filtering can be carried out in four dimensions. In this case one thus has an output image volume for the filtering a sequence of image volumes present which correspond to different measurement times. If what has been described in relation to three-dimensional filtering is applied to four-dimensional filtering it is true that for a temporal noise reduction filtering the temporal sharpness is retained so that no loss of temporal resolution occurs but is only averaged if only small, i.e. jumps between the individual images not caused by movement but by noise exist.

If one were to wish to carry out a four-dimensional image filtering for noise reduction subsequently to the iterative algorithm in accordance with FIG. 3, the procedure could be as follows: With the iterative algorithm not only the image volume $f^*(T8)$ is computed and also a series of further image volumes at adjacent points in time. For each point in time an iterative image reconstruction is thus carried out separately. The four-dimensional image filter for noise reduction can now run over this sequence of CT images. This would however be extremely computer-intensive. This is because, while only a single image volume, namely the noise-reduced version of the image volume $f^*(T^*)$ is output as the result image volume, a series of CT image volumes would have to be computed beforehand by means of the iterative algorithm. The iterative image reconstruction is far more computer-intensive than a conventional FBP reconstruction so that the method described would be very time-consuming.

Thus another method is used: by way of a conventional image reconstruction effort, e.g. FBP, a series of image volumes is reconstructed which correspond to the point in time $T^*$ and adjacent points in time. The number of points in time and thus the images needed depend in this case on the size of the four-dimensional image filter. Subsequently these image volumes will be processed with the four-dimensional image filter. As a result image a low-noise image $f^{**}(T^*)$ is available at time $T^*$, which has reduced noise both inherently and in the time dimension. Since a conventional image reconstruction method has been applied, the image $f^{**}(T^*)$ contains artifacts however because of the non-exact reconstruction. These involve the cone beam and spiral artifacts already mentioned.

This method of operation is presented in the flow diagram of FIG. 4. Each image stack in this figure corresponds to a three-dimensionally reconstructed image volume. On the left side within the dotted outline a series of image stacks can be seen, which have been reconstructed in a conventional manner and which correspond to the different times $T_1$ to $T_L$. In the middle of the times lies the time $T^*$. This time series of image volumes is subjected to four-dimensional noise-reduction filtering 4D-Reg, from which the image $F^{**}(T^*)$ results.

On the right side within the dotted outline the dataset $p_{in}(T^*)$ can be seen, from which in accordance with the procedure of FIG. 3 the image f*(T*) is reconstructed. An iterative reconstruction thus takes place for only one dataset.

Thus the two images f*(T*) and f**(T*) of time T* are present, which have complementary properties to each other: While image f*(T*) is free from artifacts but is noisy however, image f**(T*) is affected by artifacts, but has low noise. To transfer the positive properties of the two images into one result image f(T*) a combination of the two images f*(T*) and f**(T*) is carried out.

The combination of the two images f*(T*) and f**(T*) is therefore possible because the use of the modified measurement data means that the image f*(T*) has a gray value characteristic which approximately corresponds to that of the image f**(T*). This is guaranteed by a suitable choice of the CT filter kernel I in the calculation of the modified measurement data in accordance with formula (3). This should match the filter kernel used for conventional reconstruction from which the image f**(T*) results.

In this combination of the two images F*(T*) and f**(T*) use is made of the fact that artifacts which are caused by the non-exactness of the reconstruction operator, are largely low-frequency. This thus relates to the artifacts of the image f**(T*). A highpass filtering highpass of the image f**(T*) is thus carried out. This filtering is undertaken in the frequency range, i.e. the image f**(T*) is first Fourier transformed before the highpass filtering highpass is carried out.

The image f*(T*) is filtered with the lowpass filter lowpass complementary to the highpass filter highpass. Complementarity of the two filter functions means in this case that their sum amounts to 1 at each frequency.

While the highpass filter highpass and the lowpass filter lowpass are shown one-dimensionally in FIG. 4, because of the dimensions of the images f*(T*) and f**(T*), three-dimensional filters are involved.

The high frequency band obtained after the highpass filtering high pass of f**(T*) is combined with the low frequency band of f*(T*) complementary hereto, which is indicated by the + sign in FIG. 4. This combination is undertaken by simple or weighted pixel-by-pixel addition of the two frequency space images. After the combination an inverse Fourier transformation is carried out to transfer the combination image from the frequency space into the location space. In this way the results image f(T*) is obtained which is artifact-free and greatly noise-reduced.

As an alternative to the described frequency-selective combination of the two images f*(T*) and f**(T*) in the frequency space, this can also occur in the location space. For this purpose the images f*(T*) and f**(T*) are lowpass filters in the location space, from which the lowpass filtered versions f*$_{low}$(T*) and f**$_{low}$(T*) result. The combined image f(T*) is produced in the event of a simple addition over:

$$f(T^*)=(f^{**}(T^*)-f^{**}{}_{low}(T^*))+f^*{}_{low}(T^*).$$

Thus a CT image has been iteratively reconstructed in an efficient manner, with noise reduction being dispensed with during the iterations. To bring about a noise reduction of the resulting image, not only in three but in four dimensions, a four-dimensional filtering is applied to CT images obtained in the conventional manner. By a suitable application of highpass and lowpass filtering the positive properties of the different reconstruction methods, namely the artifact freedom in the iterative reconstruction and the low noise properties in the conventional reconstruction with subsequent four-dimensional filtering, can be combined with each other and thus transferred into the result image.

The invention has been described above using an example embodiment. It goes without saying that numerous changes and modifications are possible without departing from the framework of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject, matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstruction of image data of an object under examination from measurement data,
the measurement data having been captured during a relative rotational movement between a radiation source of a computed tomography system and the object under examination, the method comprising:
computing first image data by
modifying the measurement data to obtain a specific gray value characteristic of the first image data to be reconstructed, and
computing the first image data by way of an iterative algorithm using the modified measurement data; and
computing second image data by
reconstructing a series of chronologically-consecutive images, and
reducing temporal noise of the series of reconstructed images to form the second image data; and
combining the first and the second image data.

2. The method as claimed in claim 1, wherein, in the computing of the first image data by way of an iterative algorithm, no computing step for noise reduction is used during the interations.

3. The method according to claim 2, wherein the first image data relates to a specific time, the sequence of chronologically-consecutive images relates to a number of times encompassing the specific time, and the second image data relates to the specific time.

4. The method as claimed in claim 2, wherein, in the iterative algorithm, image data is initially computed from the original measurement data, and image data of the following iterations is computed using the modified measurement data.

5. The method as claimed in claim 2, wherein, in the iterative algorithm, during each iteration, measurement data is computed from computed image data and is compared with the modified measurement data.

6. The method according to claim 1, wherein the first image data relates to a specific time, the sequence of chronologically-consecutive images relates to a number of times encompassing the specific time, and the second image data relates to the specific time.

7. The method as claimed in claim 1, wherein the series of chronologically-consecutive images is computed by way of a non-iterative image reconstruction algorithm.

8. The method as claimed in claim 1, wherein, in the computation of the first image data in the modification of the measurement, a CT convolutional kernel specifying the specific gray value characteristic is used.

9. The method as claimed in claim 8, wherein the specific gray value characteristic is matched to a gray value characteristic of the second image data.

10. The method as claimed in claim 1, wherein, the processing reducing temporal noise comprises a four-dimensional non-linear filtering.

11. The method as claimed in claim 1, wherein, before the combining, the first image data is subjected to lowpass filtering and the second image data to highpass filtering.

12. The method as claimed in claim 1, wherein, for the combining, the first image data and the second image data are added pixel-by-pixel.

13. The method as claimed in claim 1, wherein, in the iterative algorithm, image data is initially computed from the original measurement data, and image data of the following iterations is computed using the modified measurement data.

14. The method as claimed in claim 1, wherein, in the iterative algorithm, during each iteration, measurement data is computed from computed image data and is compared with the modified measurement data.

15. The method as claimed in claim 14, wherein correction data is computed from the comparison and used to correct the image data.

16. A computer program stored on a non-transitory computer readable medium comprising program code for carrying out the method as claimed in claim 1 when the computer program is executed on a computer.

17. A computer program product, comprising a program code of a computer program stored on a a non-transitory computer-readable data carrier, to execute the method as claimed in claim 1 when the computer program is executed on a computer.

18. A tangible non-transitory computer readable medium including program segments for, when executed on a computer device, causing the computer device to implement the method of claim 1.

19. A control and processing unit for reconstruction of image data of an object under examination from measurement data of a CT system, comprising:
a program memory to store program code, the program code, when run on the control and processing unit,
computing first image data by
modifying the measurement data to obtain a specific gray value characteristic of the first image data to be reconstructed, and
computing the first image data by way of an iterative algorithm using the modified measurement data; and
computing second image data by
reconstructing a series of chronologically-consecutive images, and
reducing temporal noise of the series of reconstructed images to form the second image data; and
combining the first and the second image data.

20. A CT system comprising a control and processing unit as claimed in claim 19.

* * * * *

UNITED STATES PATENT AND TRADEMARK OFFICE
CERTIFICATE OF CORRECTION

PATENT NO. : 8,600,137 B2
APPLICATION NO. : 13/111244
DATED : December 3, 2013
INVENTOR(S) : Herbert Bruder It is certified that error appears in the above-identified patent and that said Letters Patent is hereby corrected as shown below:

Title page, item (75) should read as follows:

(75) Inventors: Herbert Bruder, Höchstadt (DE);
Rainer Raupach, Heroldsback (DE);
Karl Stierstorfer, Erlangen (DE)

Signed and Sealed this
Fourth Day of March, 2014

Michelle K. Lee
*Deputy Director of the United States Patent and Trademark Office*